United States Patent [19]

Weber et al.

[11] 4,057,541

[45] Nov. 8, 1977

[54] METHOD FOR ISOLATION OF 3-HYDROXY STEROIDS AND 3-KETO STEROIDS

[75] Inventors: Alfred Weber; Rudolf Müller; Johannes Kurzidim, all of Berlin, Germany

[73] Assignee: Schering Aktiengesellschaft, Berlin and Bergkamen, Germany.

[21] Appl. No.: 699,790

[22] Filed: June 25, 1976

[30] Foreign Application Priority Data

June 30, 1975 Germany .............................. 2529521

[51] Int. Cl.² .............................................. C07J 71/00
[52] U.S. Cl. ....................... 260/239.55 A; 260/397.25; 260/397.3; 260/397.4
[58] Field of Search .................. 260/397.25, 239.55 A

[56] References Cited

U.S. PATENT DOCUMENTS

| | | | |
|---|---|---|---|
| 3,450,541 | 6/1969 | Schwartz et al. | 260/397.25 |
| 3,983,147 | 9/1976 | Senda et al. | 260/397.25 |

Primary Examiner—Elbert L. Roberts
Attorney, Agent, or Firm—Millen & White

[57] ABSTRACT

An improved process for isolating 3-hydroxy steroids and 3-keto steroids from mixtures thereof with lipids by dissolving the mixtures in an organic solvent, mixing the dissolved mixture with a metal salt to form insoluble adducts of the steroids, separating the insoluble adducts and splitting the adducts to regenerate the free steroids, which comprises using methyl isobutyl ketone and/or methyl n-amyl ketone as the solvent and calcium bromide as the metal salt.

9 Claims, No Drawings

METHOD FOR ISOLATION OF 3-HYDROXY STEROIDS AND 3-KETO STEROIDS

BACKGROUND OF THE INVENTION

This invention relates to a method for isolating 3-hydroxy steroids and 3-keto steroids from mixtures thereof with lipids.

Various methods for isolating steroids from such mixtures are known. For example, in German Pat. No. 827,199, a method for isolation of sterols from mixtures is described wherein the mixture is dissolved, preferably in a hydrocarbon solvent, and is heated with a four- to sixteen-fold excess of anhydrous zinc chloride. After cooling of the solution, the precipitated ZnCl-sterol adduct can be separated out and split into the individual components. British Pat. No. 1,164,769 describes a method for the isolation of sterols from mixtures wherein the mixture is dissolved, preferably in a hydrocarbon solvent, the solution is mixed with an aqueous solution of a metal salt which is suitable for complex formation, the water is progressively removed by azetropic distillation, and the precipitated adduct is isolated and split in a conventional manner after cooling of the mixture.

Such known methods have the disadvantage that they are technically very costly on account of the high reaction temperature (customarily over 100° C.) and that in the isolation of many 3-hydroxy steroids and 3-oxo steroids considerable loss of product is experienced, since these steroids are destroyed under these conditions. In addition, these known methods often have the disadvantage that the recovery of the metal salt used for formation of the adduct, which is necessary in a method carried out on large scale simply with regard to environmental considerations, is often very costly. The technical scale use of hydrocarbon solvents is also not without its drawbacks, since these are rapidly electrostatically discharged, often have a low ignition point and are often very toxic.

Accordingly, there is a need for a method of isolating 3-hydroxy steroids and 3-keto steroids from mixtures containing such compounds without the disadvantage of the known methods.

OBJECTS OF THE INVENTION

Accordingly, it is a general object of this invention to provide an improved process for the purification and recovery of 3-hydroxy steroids and 3-keto steroids.

Another object of this invention is to provide such a process which gives good yields even when employed at relatively low temperatures.

A further object of this invention is to provide such a process which is highly economical and environmentally sound for use on a commercial scale.

Upon further study of the specification and appended claims, further objects and advantages of this invention will become apparent to those skilled in the art.

SUMMARY OF THE INVENTION

Briefly, the above and other objects, features and advantages of the present invention are attained by providing, in a process for the isolation of 3-hydroxy steroids and 3-keto steroids from mixtures thereof with lipids by dissolving the mixtures in a hydrocarbon solvent, mixing the dissolved mixture with a metal salt to form an insoluble adduct of the steroids and the metal salt, separating the insoluble adducts and splitting the adducts to regenerate the free steroids, the improvement which comprises employing methyl isobutyl ketone, methyl n-amyl ketone or a mixture thereof as the solvent and calcium bromide as the metal salt.

DETAILED DISCUSSION

In the process of this invention, a solution of a mixture of one or more 3-hydroxy steroids and 3-keto steroids and lipids in methyl isobutyl ketone or methyl n-amyl ketone, or mixtures thereof, is mixed with calcium bromide or a solution of calcium bromide in methyl isobutyl ketone or methyl n-amyl ketone, or mixture thereof, and the precipitated adduct separated and split in a known manner. The use of solvents other than methyl isobutyl ketone or methyl n-amyl ketone does not lead to the same results, according to the results of present research. Calcium bromide (in its hydrate form) is relatively soluble in alcohols such as methanol, ethanol, isopropanol, propane-1,3-diol or hexane-1-ol; but if such solutions are added to a steroid solution in the same solvent (the use of a mixture of solvents is almost always more costly with regard to recovery than the use of only one solvent), then little or no quantitative precipitation occurs. In other tested ketones, including acetone, methyl ethyl ketone, diethyl ketone, diisobutyl ketone and methyl isopropyl ketone, calcium bromide is so poorly soluble that these ketones are not suitable for causing the named steroids to precipitate out of a primary homogenous phase. Nonpolar solvents, e.g., benzene, are also not suitable, on account of the low solubility of calcium bromide in these solvents.

The use of other metal salts which are otherwise suitable for adduct formation also leads to poorer results as compared to the method of the present invention, presumably because these metal salts are too poorly soluble in methyl isobutyl ketone or methyl n-amyl ketone (as for example calcium chloride) or because the adducts formed in these ketones have too great a solubility for quantitative precipitation therefrom.

Preferably, an amount of solvent is employed which provides a solution with about 0.5% to 50%, preferably about 5% to 50%, by weight steroid content, which is then mixed at a temperature of 0° to 50° C., preferably about room temperature, with calcium bromide (preferably in a hydrate form) or a solution thereof, e.g., from about 5%, preferably from about 10%, to about 35% calcium bromide (preferably in a hydrate form) in methyl isobutyl ketone, methyl n-amyl ketone or a mixture thereof. The adduct which is formed is isolated in a conventional manner after the steroid adduct precipitates, e.g., by filtration, and is split, e.g., by its introduction into water or an alcohol such as methanol or ethanol. In the adduct reaction, preferably about 2 to 10 molar equivalents of calcium bromide are used per Mol of precipitating steroid.

The excess calcium bromide can thereafter be removed in a simple manner from the methyl isobutyl ketone or methyl n-amyl ketone by extraction with water.

The aqueous calcium bromide solutions can then be used again to form the adducts, after concentration and extraction.

With the process of this invention, it is simple to isolate phytosterols, e.g., campesterol, stigmasterol, sitosterol, diosgenin, brassicasterol, ergosterol or hecogenin, from the plant extracts containing these compounds or their residues and hydrolysates. Likewise, steroid alkaloids, e.g., solasodol, or zoosterols, e.g., cholesterol, can be isolated from lipid fractions of vegetable or animal origin or their hydrolysates which contain these compounds.

The term "lipids" as used herein mean water-insoluble, hydrophobic solvent-soluble non-steroidal compounds and steroids other than 3-hydroxy steroids and 3-oxo steroids.

The method according to the invention is furthermore of importance for the isolation of 3-keto steroids, e.g., 4-androsten-3,17-dione, 1,4-androstadiene-3,17-dione, testosterone, hydrocortisone, cortisone, progesterone, 17α-hydroxyprogesterone, prednisolone, 17α-acetoxyprogesterone, etc., from extracts of microbiological steroid conversions or from concentrations of extracts of that type.

Without further elaboration, it is believed that one skilled in the art can, using the preceding description, utilize the present invention ot its fullest extent. The following preferred specific embodiments are, therefore, to be construed as merely illustrative and not limitative of the remainder of the disclosure in any way whatsoever. In the following examples, all temperatures are set forth uncorrected in degrees Celsius; unless otherwise indicated, all parts and percentates are by weight.

The purity data quoted in the Examples are obtained from the products by gas chromatography or thin layer chromatography.

EXAMPLE 1 a. 53,5 g. of fatty acid distillate residue with a sterol content of 26.4% (consisting of campesterol, stigmasterol and sitosterol) are dissolved in 140 ml. of methyl isobutyl ketone and mixed with 60 ml. of 30% methyl isobutyl ketone solution of calcium chloride dihydrate, with stirring.

The mixture is left for 16 hours at room temperature, the resultant precipitate if filtered out, washed with diisopropyl ether and dried at 60° C. in a vacuum to yield 20.0 g. of the sterol adduct.

b. The resultant adduct is added to 200 ml. water, the mixture is stirred for one hour, the precipitated sterol mixture is filtered out, washed with water and dreid at 60° C. in a vacuum to yield 14.6 g. of a mixture of campesterol, stigmasterol and sitosterol, with a purity of 87.5% (90.3% of the theoretical).

EXAMPLE 2 a. 25 ml. of 30% methyl isobutyl ketone solution of calcium bromide dihydrate are added to a solution of 75.0 g. of soya oil fraction with a sterol content of 6.8% (consisting of campesterol, stigmasterol and sitosterol) in 60 ml. methyl isobutyl ketone.

The mixture is left overnight, the precipitated adduct is filtered out, washed with diisopropyl ether and dried in a vacuum at 60° C. to yield 7.70 g. of the sterol adduct.

b. The resultant adduct is split under the conditions described in Example 1b and concentrated to yield 4.67 g. of a mixture of campesterol, stigmasterol and sitosterol, with a purity of 95.0% (86.4% of theoretical).

EXAMPLE 3 a. 32 g. of calcium bromide dihydrate are added to a solution of 89.5 g. soya oil fraction with a sterol content of 6.8% (consisting of campesterol, stigmasterol and sitosterol), in of methyl isobutyl ketone and the mixture is stirred for 16 hours at room temperature. The precipitated sterol adduct is filtered out, washed with diisopropyl ether and dried in a vacuum to yield 8.95 g. of sterol adduct.

b. The resultant sterol adduct is split under the conditions described in Example 1b concentrated to yield 5.75 g. of a mixture of campesterol, stigmasterol and sitosterol, with a purity of 89.2% (81.7% of theoretical).

EXAMPLE 4

50.0 g. of wool wax alcohols containing 30.2% cholesterol are dissolved in 150 ml. of methyl isobutyl ketone, mixed with 75 ml. of a 30% methyl isobutyl ketone solution of calcium bromide dihydrate, and the mixture is stirred for 16 hours at room temperature.

The adduct which forms is isolated and split as described in Example 1 to yield 15.7 g. of cholesterol with a purity of 91.5% (94.5% of theoretical).

EXAMPLE 5

300 ml. of a methyl isobutyl ketone extract which contains 14.2% testosterone, in addition to yeast-containing materials and silicone oil SH, is mixed with 25 ml. of a 30% methyl isobutyl ketone solution of calcium bromide dihydrate, with stirring, and kept for 16 hours at room temperature. The precipitating adduct is isolated and split under the conditions described in Example 1 to yield 4.46 g. testosterone, with a purity of 92.2% (96.4% of theoretical).

EXAMPLE 6

100 ml. of a methyl n-amyl ketone extract containing 7.86 g. of 1,4-androstadiene-3,17-dione is mixed with 60 ml. of a 30% calcium bromide dihydrate solution in methyl isobutyl ketone and stirred for 16 hours at room temperature.

The precipitated adduct is isolated and split as described in Example 1 to yield 7.58 g. of 1.4-androstadiene-3.17-dione with a purity of 95.5% (91.6% of theoretical).

EXAMPLE 7

To 100 ml of a methyl n-amyl ketone extract containing 7,86 grams of 1,4-androstadien-3,17-dione are added 120 ml of a solution of 15% strength of calcium bromide dihydrate in methyl n-amyl ketone, and the whole is stirred for 16 hours at room temperature.

The separated adduct is isolated and split up as described in Example 1, and there are obtained 7,93 grams of 1,4-androstadien-3,17-dione having a purity of 94,7% (95,8% of the theoretical yield).

EXAMPLE 8

To 100 ml of a methyl n-amyl ketone extract, which contains, in addition to yeast content substances and silicone oil SH, 6,8% of testerone, are added while stirring 75 ml of a solution 15% strength of calcium bromide dihydrate in methyl n-amyl ketone. After standing for 16 hours at room temperature, the mixture is worked up as in Example 1. There are obtained 7,0 grams of testosterone having a purity of 95,3% (=98,5% of the theoretical yield).

EXAMPLE 9

To 100 ml of a methyl n-amyl-ketone extract containing 6,1% of 1,4-androstadien-3,17-dione are added 75 ml of a solution of 15% strength of calcium bromide dihydrate in methyl n-amyl ketone, and the whole is kept overnight at room temperature.

After isolating and splitting up the adduct as in Example 1, there are obtained 6,25 grams of 1,4-androstadien-3,17-dione having a purity of 93,6% (= 95,8% of the theoretical yield).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the isolation of 3-hydroxy steroids and 3-keto steroids from a mixture thereof with lipids by dissolving the mixture in an organic solvent, mixing the dissolved mixture with a metal salt to form insoluble adducts of the steroids and a metal salt, separating the insoluble adducts, and splitting the adducts to regenerate the free steroid, the improvement which comprises employing as the solvent methyl isobutyl ketone, methyl n-amyl ketone or a mixture thereof and employing calcium bromide as the metal salt.

2. A process according to claim 1, wherein the steroid mixture is dissolved to a concentration of about 5 to 50% by weight in either methyl isobutyl ketone or methyl n-amyl ketone.

3. A process according to claim 1, wherein a solution of about 10-35% by weight calcium bromide in either methyl isobutyl ketone or methyl n-amyl ketone thereof is added to a solution of the steroid and lipids in the same solvent.

4. A process according to claim 3, wherein the adducts are formed at about room temperature.

5. A process according to claim 1, wherein the isolated steroid is a phytosterol or mixture of phytosterols.

6. A process according to claim 1, wherein the isolated steroid is a steroid alkaloid.

7. A process according to claim 1, wherein the isolated steroid is a 3-keto steroids.

8. A process according to claim 3 wherein the steroid mixture is dissolved to a concentration of about 5 to 50% by weight in either methyl isobutyl ketone or methyl n-amyl ketone and the adducts are formed at about room temperature.

9. A process according to claim 1 wherein about 2 to 10 molar equivalents of calcium bromide per mole of precipitated steroid is employed to form the adducts and the excess is isolated from the solvent after separation of the insoluble adducts therefrom by extraction of the solvent with water and used again to form adducts with one or more 3-hydroxy steroids and 3-keto steroids in another mixture with lipids.

* * * * *